United States Patent [19]

Shimenkov

[11] Patent Number: 4,577,649
[45] Date of Patent: Mar. 25, 1986

[54] TOOTHPICK

[76] Inventor: Marat Shimenkov, 65-46 Parson Blvd., #2A, Flushing, N.Y. 11365

[21] Appl. No.: 145,690

[22] Filed: May 1, 1980

[51] Int. Cl.⁴ .............................................. A61C 15/00
[52] U.S. Cl. ......................................... 132/93; 132/89
[58] Field of Search .............................. 132/89, 90, 93

[56] References Cited

U.S. PATENT DOCUMENTS

| | | | |
|---|---|---|---|
| 1,996,205 | 4/1935 | Jackson | 132/89 |
| 1,997,877 | 4/1935 | Spanel | 132/89 |
| 2,477,194 | 7/1949 | Millard | 132/93 |
| 3,050,072 | 8/1962 | Ditner | 132/93 |
| 3,141,466 | 7/1964 | Fleming | 132/93 |
| 3,672,378 | 6/1972 | Silverman | 132/93 |
| 4,040,433 | 8/1977 | Edison | 132/89 |

FOREIGN PATENT DOCUMENTS

| | | | |
|---|---|---|---|
| 19504 | of 1912 | United Kingdom | 132/89 |
| 627654 | 8/1949 | United Kingdom | 132/93 |

Primary Examiner—Paul J. Hirsch
Attorney, Agent, or Firm—Ilya Zborovsky

[57] ABSTRACT

A toothpick has two side faces which are inclined relative to one another so as to form an acute angle therebetween and a sharp upper edge, and a third face which connects the side faces with one another and forms two sharp lower edges. The toothpick may be elastic in transverse direction. It may be solid, hollow or composed of two connected strips.

10 Claims, 7 Drawing Figures

TOOTHPICK

BACKGROUND OF THE INVENTION

The present invention relates to a toothpick.

Many toothpicks have been proposed and are widely utilized. Known toothpicks have circular or square cross sections. Such toothpicks possess essential disadvantages. It is known that a gap between two adjacent teeth has a triangular cross section. This means that the cross section of the known toothpicks do not correspond to the cross section of the above mentioned gap. When the known toothpicks are utilized for cleaning purposes to remove remaining particles of food, the toothpick does not abut against the proximal faces of two adjacent teeth and thereby the cleaning is performed not effectively. Moreover, the fact that the cross section of the toothpick does not correspond to the cross section of the gap leads to irritation and injury of a gum projection between two adjacent teeth. The known toothpick also does not have rear sharp edges and thereby it cannot penetrate into the lower portions or pockets of the gap which also results in insufficient cleaning action.

SUMMARY OF THE INVENTION

Accordingly, it is an object of the present invention to provide a toothpick which avoids the disadvantages of the prior art.

More particularly, it is an object of the present invention to provide a toothpick which provides for better action in cleaning gaps between teeth and removing remaining particles of food.

In keeping with these objects and with others which will become apparent hereinafter, one feature of the present invention resides, briefly stated, in a toothpick which has a body portion with two side faces extending in a direction of elongation and inclined relative to one another so as to form an acute angle therebetween, and a third face which connects the two faces with each other and is concave.

When the toothpick is designed in accordance with the present invention, it has a cross section which substantially corresponds to the cross section of the gap between two adjacent teeth. When such a toothpick is inserted between the teeth and displaced within the gap, it positively abuts against the proximal faces of the two adjacent teeth by its inclined end faces and thereby cleans these surfaces and removes remaining particles of food from the entire cross section of this gap. Moreover, the lower or third concave face forms two sharp edges at this face near the lower ends of the side faces. These sharp edges penetrate into the lower regions or pockets of the gap and clean the latter as well.

The novel features of the present invention which are considered characteristic for the same, are set forth in the appended claims. The invention itself, however, both as to its construction and its manner of operation will be best understood from the following description of preferred embodiment taken together with the accompanying drawing.

DESCRIPTION OF PREFERRED EMBODIMENTS

Figure 1:
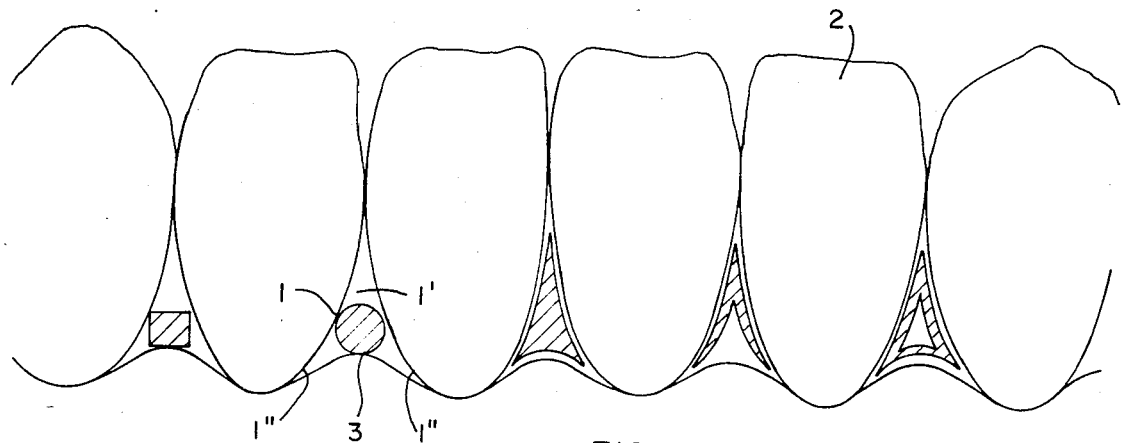
FIG. 1 is a view showing two adjacent teeth and a gap therebetween in which two known toothpicks and three toothpicks in accordance with the present invention are inserted.

As shown in FIG. 1, a gap 1 between two adjacent teeth 2 has a triangular cross section. The gap 1 has a sharp upper end portion and two sharp lower end portions 1''. The above-mentioned sharp portions has cross sections which decreases in respective directions. The gap 1 has a lower end face which is concave downwardly, inasmuch as it is formed by a convex projection 3 between the teeth. As shown in FIG. 1, neither the square toothpick nor the circular toothpick correspond to the shape of the gap 1.

A toothpick in accordance with the invention has a body which is identified by reference numeral 4 in toto. The inventive toothpick or more particularly its body 4 has two side faces 5 which extend in direction of elongation of the body are are inclined relative to one another so as to form an acute angle at the upper end of the toothpick. An edge 6 which is substantially sharp is thereby formed at the upper end. On the other hand, the body portion has two lower end portions 7 each formed at the lower end of a respective one of the side faces 5.

Figures 2, 3, 4:
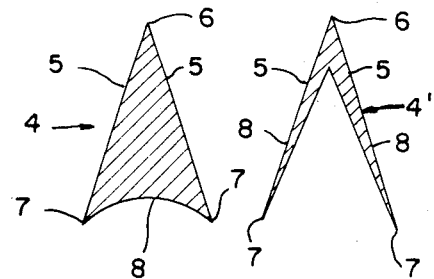
FIG. 2 is a view showing a cross section of the toothpick in accordance with one embodiment of the present invention.
FIG. 3 is a view showing the toothpick in accordance with another embodiment of the present invention.
FIG. 4 is a view showing a cross section of the toothpick in accordance with a further embodiment of the present invention.

The toothpick shown in FIG. 2 has a solid uninterrupted cross section. The body of this toothpick is formed as a trihedral body. The lower face 8 of the trihedral body is inwardly concave. Thereby, the two lower edges 7 are formed which are sharp. At the same time the lower face 8 has the concave contour corresponding to the contour of the projection 3 of the gum between the teeth 2.

When such a toothpick is inserted into the gap 1 and displaced in the latter, the body overlaps the entire cross section of the gap 1 and removes extraneous matter from the gap in the central region, and also in the regions 1' and 1'' by the sharp edges 7. The body 4 of the toothpick may be constituted of an elastic material so that it can be compressed when it is introduced into the gap of a slightly smaller cross section. This also provides for firm abutment of the faces 5 of the toothpick against the proximal faces of the two adjacent teeth. At the same time, the toothpick may be utilized for cleaning the gaps of different cross sectional areas.

The toothpick shown in FIG. 3 has a body 4' which is formed by two strips 8 connected with one another along one of their edges so as to form the upper edge 6 and two lower edges 7. The latter are formed since the lower face of the body is again concave, this time to a greater extent than the concave face of the toothpick of FIG. 2. The toothpick of FIG. 3 or its body 4' is also deformable in direction transverse to the direction of elongation and to the side faces of the toothpick. Again, the edges 7 can clean the gum pockets 1' and 1", e.g. gaps between a tooth surface and a freely adjoining portion of the gum.

As shown in FIG. 3, the toothpick formed by the two strips 8 may be of cross section which reduces toward the insertion end of the body. When the body 4' is introduced into the gap 1, starting from the insertion end 9, it is gradually compressed in the transverse direction. The walls of the body of the toothpick of FIG. 4 may also have a reducing cross section.

The body 4 or 4' is connected with a handle 10 which is to be grasped by a user so as to introduce the body into the gap between the teeth. Whereas the body has a cross section increasing in direction toward the lower end, the handle may be of a constant cross section.

The body 4" of the toothpick shown in FIG. 4 is hollow. This results in that the body 4" is elastically deformable in the transverse direction, and also in that such a body may be filled with toothpaste, medications and the like. When the inner hollow 11 of this body portion 4" has an outlet opening, for example, at the side faces of the same, the above-mentioned substances may be expelled from the hollow 11 by squeezing of the body.

The toothpicks shown in the above-listed figures may also have a thin projection which extends upwardly from the upper sharp edge of the body.

Figures 5, 6:
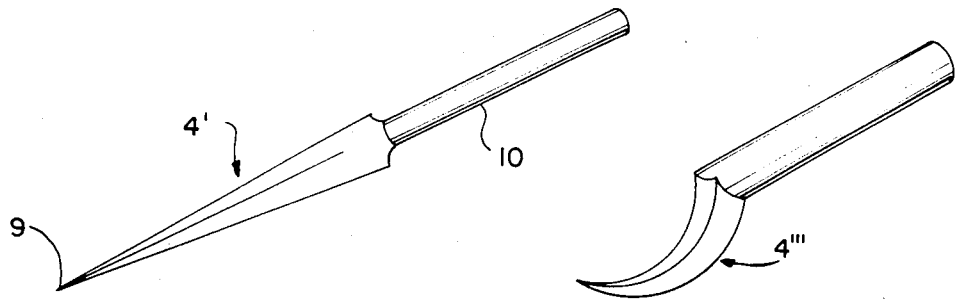
FIG. 5 is a perspective view of the toothpick in accordance with FIG. 3.
FIG. 6 is a view showing a perspective view of the toothpick in accordance with still a further embodiment of the invention.

The toothpick of FIG. 6 has a body 4''' which is crescent-shaped, whereas the handle 10 may be straight. When the body portion is crescent-shaped, it moves during the insertion into the gap along a curve and does not injure the projection and sides of the gum. Since the handle extends in a plane which is different as compared with the plane of the body 4''' and is offset relative to the latter, the toothpick can be displaced in the gap 1 without contacting a lip of the user.

Figure 7:
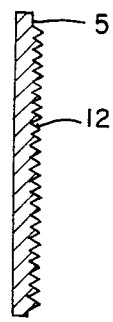
FIG. 7 is a view showing a portion of the toothpick in accordance with an additional embodiment of the invention.

The toothpick in accordance with the present invention effectively removes remaining particles of food from the gap and its pockets. However, this capability of the toothpick may be further increased by the provision on the side faces 5 of the body, texture of structure. For example, nap may be formed on the side faces 5, as identified by reference numeral 11 in FIG. 7. The nap can remove not only food, but also materia alba and plaque which could otherwise be converted into toothstone. The nap can also hold a toothpaste and liquids as well as medications so that they can be introduced into the gap or rubbed into the tooth faces. Deodorants, antiseptics, prophypastes, anaesthetics and the like can also be introduced by the nap.

The toothpick especially for introducing the above-mentioned substances may be provided with a hermetic packing in which it is contained together together with the substances to be introduced.

The invention is not intended to be limited to the details shown, since various modifications and structural changes are possible without departing in any way from the spirit of the present invention.

What is claimed to be new and intended to be protected by Letters Patent is set forth in particular in the appended claims.

I claim:

1. A toothpick, comprising
an elongated trihedral hollow body having two side walls forming two straight faces extending in direction of elongation and inclined relative to one another so as to form an acute angle therebetween, said body also having a third wall which connects said first-mentioned side walls with one another and defines a third face which is concave so as to form two lower edges which are substantially sharp, said body being elastic in direction transverse to the direction of elongation so as to be compressed during insertion of the toothpick between teeth whereby said straight side faces act upon the teeth, and said third wall being upwardly convex so as to elastically urge said side walls in the transverse direction away from one another and thereby against the teeth.

2. A toothpick as defined in claim 1, wherein said strips are elastically displaceable in a direction which is transverse to the direction of elongation and to said side faces.

3. A toothpick, comprising
an elongated body having two side faces extending in direction of elongation and inclined relative to one another so as to form an acute angle therebetween, said body also having a third face which connects said first-mentioned side faces with one another, said third face being concave so as to form two lower edges which are substantially sharp, said body being formed by two strips each forming a respective one of said side faces and a respective one of said lower edges, each of said strips having a first end section forming the respective lower edge and a second end section connected with the second end section of the other strip, said body formed by said two strips being elastic in direction transverse to the direction of elongation.

4. A toothpick as defined in claim 1, wherein said trihedral body has an upper end, and a lower end wherein said end face and said lower edges are formed, said side faces together forming an upper edge at said upper end, which is substantially sharp.

5. A toothpick as defined in claim 1, wherein said side faces of said body are textured.

6. A toothpick as defined in claim 1, and further comprising a handle which is connected with said body and also extends in the direction of elongation.

7. A toothpick as defined in claim 1, wherein said side faces of said body are provided with nap.

8. A toothpick as defined in claim 1, wherein said body portion is crescent-shaped.

9. A toothpick as defined in claim 8, and further comprising a substantially straight handle connected with said crescent-shaped body.

10. A toothpick as defined in claim 1, wherein each of said strips has a thickness decreasing from the second end portion to the first end portion of the same strip.

* * * * *